(12) United States Patent
Larking et al.

(10) Patent No.: US 7,116,422 B2
(45) Date of Patent: Oct. 3, 2006

(54) WAVELENGTH MODULATION SPECTROSCOPY METHOD AND SYSTEM

(75) Inventors: Rikard Larking, Floda (SE); Stefan Lundqvist, Askim (SE); Per-Arne Thorsén, Öjersjö (SE)

(73) Assignee: Siemens Aktiengesellschaft, Munich (DE)

( * ) Notice: Subject to any disclaimer, the term of this patent is extended or adjusted under 35 U.S.C. 154(b) by 248 days.

(21) Appl. No.: 10/925,203

(22) Filed: Aug. 24, 2004

(65) Prior Publication Data

US 2005/0046852 A1    Mar. 3, 2005

(30) Foreign Application Priority Data

Aug. 28, 2003    (EP) .................. 03019448

(51) Int. Cl.
*G01N 21/61*    (2006.01)
(52) U.S. Cl. .................................................. 356/437
(58) Field of Classification Search ................ 356/432, 356/436–439; 250/343
See application file for complete search history.

(56) References Cited

U.S. PATENT DOCUMENTS

| 6,040,914 | A | 3/2000 | Bortz et al. |
| 6,351,309 | B1 * | 2/2002 | Bomse et al. ............... 356/437 |
| 6,356,350 | B1 | 3/2002 | Silver et al. |
| 6,611,335 | B1 | 8/2003 | Hovde |
| 6,940,599 | B1 * | 9/2005 | Hovde ........................ 356/432 |

OTHER PUBLICATIONS

Pawel Kluczynski and Ove Axner, Theoretical description based on Fourier analysis of wavelength-modulation spectrometry in terms of analytical and background signals, Applied Optics, vol. 38, No. 27, Sep. 1999, pp. 5803-5815.

* cited by examiner

*Primary Examiner*—Richard A. Rosenberger

(57) ABSTRACT

In a wavelength modulation spectroscopy method and system the light of a tunable light source is modulated with a frequency $f_0$, while the wavelength is swept over an interaction feature of a sample to be measured. The light of the light source is passed to a sample for interacting and thereafter detected and demodulated at a higher harmonic $Nf_0$.

To suppress effects of fluctuations of the optical transmission of the system on the measurement, originating from varying dust loads, high temperature, gas turbulence etc. in the measurement path (3), a burst signal in form of an envelope modulated pilot tone is added to the modulation of the light (1) of the light source (2) synchronously with the wavelength sweeps at a wavelength outside the interaction feature of the sample. The injected burst signal is at the detection frequency $Nf_0$, where $N \geq 2$, and is detected together with the measured spectrum from the sample and act as absorption normal, which the spectrum can be calibrated against.

6 Claims, 2 Drawing Sheets

WAVELENGTH MODULATION SPECTROSCOPY METHOD AND SYSTEM

CROSS REFERENCE TO RELATED APPLICATIONS

This application claims priority to the European application No. 03019448.4, filed Aug. 28, 2003 and which is incorporated by reference herein in its entirety.

FIELD OF INVENTION

The invention relates to a wavelength modulation spectroscopy method. It further relates to a wavelength modulation spectroscopy system.

BACKGROUND OF INVENTION

In wavelength modulation spectroscopy (WMS) the wavelength and the intensity of the light of a tunable light source, usually a continuously tunable laser such as a diode laser, is modulated with a frequency $f_0$, while the wavelength is swept over an interaction feature of a sample to be measured, for example a molecular absorption line in a gas sample. As the light interacts with the sample, for example propagates through a gas sample, wavelength dependent interaction such as absorption converts some of the wavelength modulation into an intensity modulation of the light. Thus, the light will have an overtone spectrum generated by the interaction process, the harmonic content of the spectrum being dependent on the interaction feature, for example the width and shape of the molecular absorption line in the gas and the etalons in the system. When the light then impinges onto a measuring detector, for example a photodiode, the measuring detector output contains AC components at the modulation frequency $f_0$ and its higher harmonics $Nf_0$ (N=2, 3, 4, etc.). Demodulating the measuring detector output at one of said higher harmonics $Nf_0$ shifts the measurement from frequencies near DC, where the light source is noisy, into a higher frequency range, where the noise is lower, thus improving the measurement sensitivity.

In difficult measurement conditions, however, the light may be further modulated by a time dependence of the optical transmission of the system. An example are in-situ measurements of trace gas constituents in combustion environments, where varying dust loads, high temperature, gas turbulence etc. modulate the light in the kHz range.

SUMMARY OF INVENTION

Therefore, the invention seeks to provide a wavelength modulation spectroscopy method and system, which effectively compensate such transmission variations.

According to the invention this is achieved by the claims.

Preferred embodiments of the method and the system according to the invention are specified in the dependent claims.

The approach in this invention is to calibrate or normalize the measurement by adding a burst signal in form of an envelope modulated pilot tone to the modulation of the tunable light source synchronously with the wavelength sweeps at a wavelength outside the interaction feature of the sample. The injected burst signal is at the detection frequency $Nf_0$, where $N \geq 2$, and is detected together with the measured spectrum from the sample and act as absorption normal, which the spectrum can be calibrated against. The injected burst signal will also continuously calibrate the amplitude and phase response of the electronic signal chain of the system compensating for any changes due to temperature and aging of the components of the system.

BRIEF DESCRIPTION OF THE DRAWING

The invention will be now described by way of a preferred example and with reference to the accompanying drawing, in which.

DETAILED DESCRIPTION OF INVENTION

Figure 1:
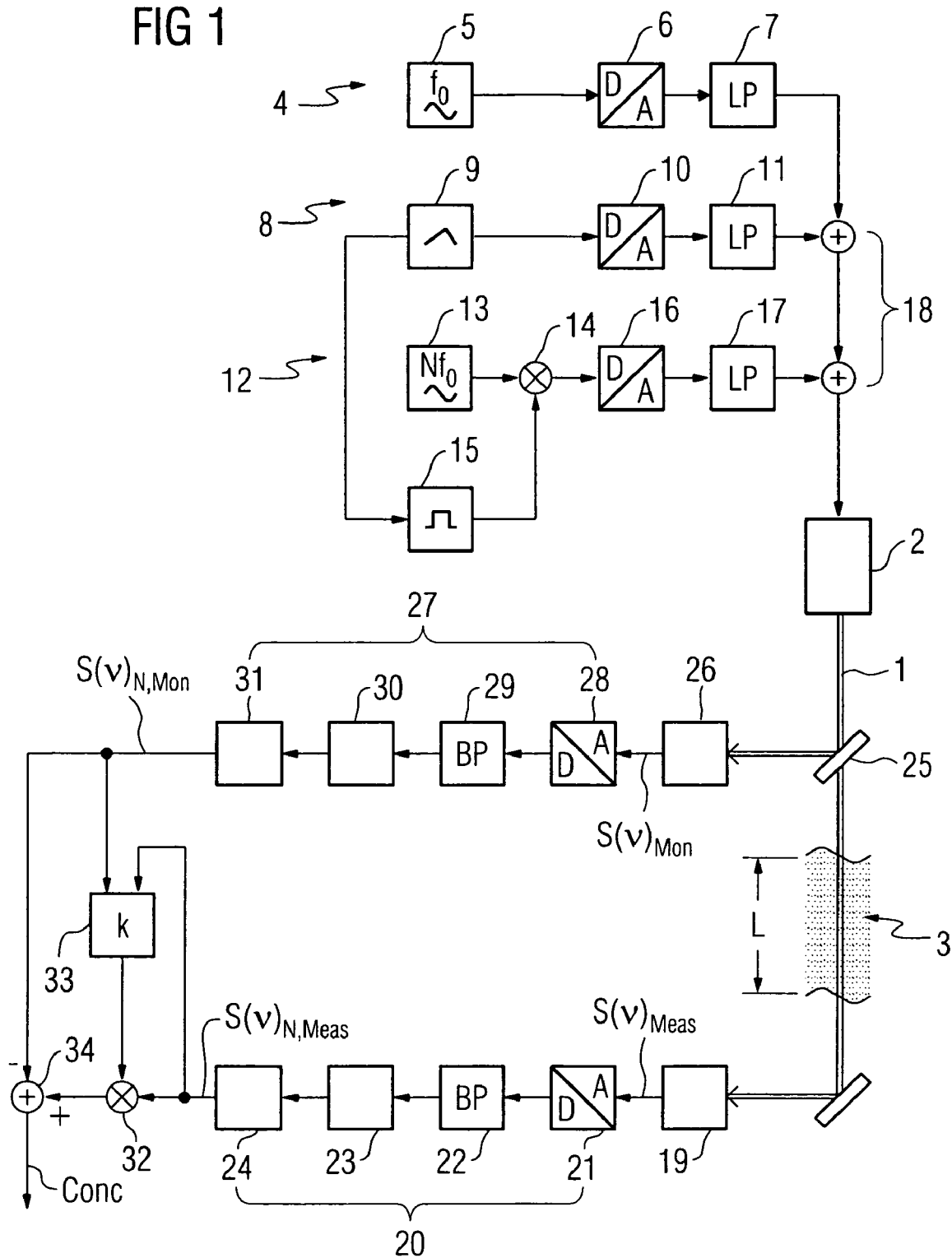
FIG. 1 shows a block diagram of the system in accordance with the invention.

For a better understanding of the following description, reference is made to Applied Optics, vol. 38, no. 7, pp. 5803–5815, September 1999, where a theoretical description of the wavelength-modulation (WM) spectrometry technique is given. In the following description the optical frequency $\nu$ is used instead of the wavelength $\lambda$, which are inversely proportional to each other.

The light 1 of a tunable light source 2, here a diode laser, is passed through a measurement path 3 for interacting with a sample, here a weakly absorbing gas sample. The light 1 is attenuated exponentially according to the Beer-Lambert law:

$$I=I_L\exp[-[\alpha_0\chi(\nu,t)+\tau(t)]L]=T(t)^L \exp[-\alpha_0\chi(\nu,t)L] \quad \text{(Equation 1)},$$

where I is the intensity of the light 1 after passing through the measurement path 3, $I_L$ is the intensity of the light 1 emitted from the light source 2, $\alpha_0$ and $\chi(\nu, t)$ represent the peak absorbance and the peak-normalized shape of a molecular absorption line of interest in the gas sample, respectively, and $T(t)=\exp[-\tau T(t)L]$ is a transmission factor over the measurement path 3 having a length L. The transmission factor T(t) stands for the wavelength independent transmission of the optical system, which transmission, however, is time dependent due to varying dust load, high temperature, gas turbulence in the measurement path 3 and contamination of optical surfaces. At atmospheric pressure the shape of the molecular absorption line is typically given by:

$$\chi(\nu, t) = \frac{1}{1 + ((\nu - \nu_0)/\gamma)^2}, \quad \text{(Equation 2)}$$

where $\nu_0$ is the line center frequency and $\gamma$ is the line width defined as half width at half maximum (HWHM).

Modulation of the light 1 of the diode laser 2 is accomplished by modulation of its injection current i, which imposes modulation on the optical frequency $\nu_L$ and to some extend on the intensity $I_L$ of the emitted light 1.

In a first modulation means 4 a digital waveform generator 5 generates a bit stream representing a sinusoidal signal at a frequency $f_0$. The bit stream is converted by a digital-to-analog converter 6 and after that filtered by a low-pass filter 7.

In a second modulation means 8 a second digital waveform generator 9 provides a bit stream representing a slow sweep function, which may be part-wise linear in time or of an arbitrary shape. It also generates an address domain defining the range for this slow sweep function. The bit stream is converted to analog form by a digital-to-analog converter 10 and after that filtered by a low-pass filter 11.

In a third modulation means 12 a third digital waveform generator 13 provides a bit stream representing a sinusoidal signal at a frequency $Nf_0$, which signal is multiplied in a multiplication means 14 by an envelope function of arbitrary shape from a digital envelope generator 15 to generate a digital burst function. The envelope function and thus the burst function are generated in dependence on and synchronously with the slow sweep function of the second digital waveform generator 9 at a predetermined position of the sweep function, where the resulting wavelength or optical frequency of the diode laser 2 is outside any absorption line in the gas sample. The digital burst function is then converted to an analog burst signal by a digital-to-analog converter 16 and a following low-pass filter 17.

The analog signals of said first, second and third modulation means 4, 8, 12 are summed in adding means 18 and fed to a modulation input of the diode laser 2. Thus, the injection current i of the diode laser 2 is given by:

$$i = i_0(t) + i_\alpha(t)\cos 2\pi f_0 t + i_p(t)\cos 2\pi N f_0 t \quad \text{(Equation 3)},$$

where $i_0(t)$ includes a bias and a slow current function, for example a slow current ramp, $i_a(t)$ is the modulation amplitude at the modulation frequency $f_0$ and $i_p(t)$ is the amplitude envelope of the burst signal at the frequency $Nf_0$.

The modulation of the injection current i of the diode laser 2 results in a modulation of the optical frequency $v_L$ of the emitted light 1:

$$v_L = v_0(t) + v_\alpha \cos 2\pi f_0 t + v_p \cos 2\pi N f_0 t \quad \text{(Equation 4)},$$

where $v_0(t)$ represents a sweep of the optical frequency over the absorption line of interest in the gas sample, $v_a$ is the amplitude of the modulation of the optical frequency at the modulation frequency $f_0$ and $v_p$ is the optical frequency modulation amplitude induced by the burst signal.

As the injection current i for modulating the light 1 of the diode laser 2 is a periodic function of time, the intensity $I_L$ of the emitted light 1 will also be a periodic function of time and therefore can be expressed in terms of a Fourier series:

$$I_L = \left[\sum_{n=0}^{\infty} I_{L,n}^e(v_L)\cos 2\pi n f_0 t + \sum_{n=0}^{\infty} I_{L,n}^o(v_L)\sin 2\pi n f_0 t\right] + \quad \text{(Equation 5)}$$

$$i_p(t)\cos 2\pi N f_0 t$$

$$\approx I_{L,0}(v_L) \cdot [1 + \kappa_1 v_a \cos(2\pi f_0 t + \phi_1) +$$

$$\kappa_2 v_a^2 \cos(2\pi 2 f_0 t + \phi_2)] + i_p(t)\cos 2\pi N f_0 t,$$

whereby $I_{L,n}^e(v_L)$ and $I_{L,n}^o(v_L)$ stand for the even and odd harmonic components of the light intensity $I_L$, respectively, generated by the applied injection current i and the non-linearity of the diode laser 2. The slow intensity variation due to the sweep of the optical frequency of the light 1 is taken as the DC term $I_{L,0}(v_L)$ and $\kappa_1$ and $\kappa_2$ are defined as the linear and the non-linear intensity modulation coefficients, respectively. As $\kappa_2$ is a very small factor, it will be neglected in the following.

According to the slow sweep function of the second digital waveform generator 9 the optical frequency of the emitted light 1 sweeps over the molecular absorption line of interest of the gas sample 18 in the measurement path 3, while the light 1 is modulated with the frequency $f_0$. Due to the wavelength dependent absorption the light 1 will have an overtone spectrum, the harmonic content of the spectrum being dependent on the width and shape of the molecular absorption line.

After passing through the measurement path 3 the light 1 impinges onto a measuring detector 19, the output of which is given by:

$$S_{Meas} = \eta_{Meas} \cdot I \quad \text{(Equation 6)},$$

where $\eta_{Meas}$ is an instrument factor of the system.

The intensity I of the light 1 impinging on the measuring detector 19 is a periodic function of time, so that it can be expressed in terms of a Fourier series as well as the line-shape function:

$$\chi(v_L, t) = \sum_{n=0}^{\infty} \chi_n^e(v_L, t)\cos 2\pi n f_0 t. \quad \text{(Equation 7)}$$

As the line-shape function $\chi(v_L, t)$ follows the modulation of the frequency without phase delay, only the cosine terms in the series expansion are needed. By inserting equations 5 and 7 into equation 1 one obtains an optical-frequency-dependent expression for the intensity $I(v)$, which expression inserted into equation 6 gives the measuring detector output $S(v)_{Meas}$.

Figure 2:
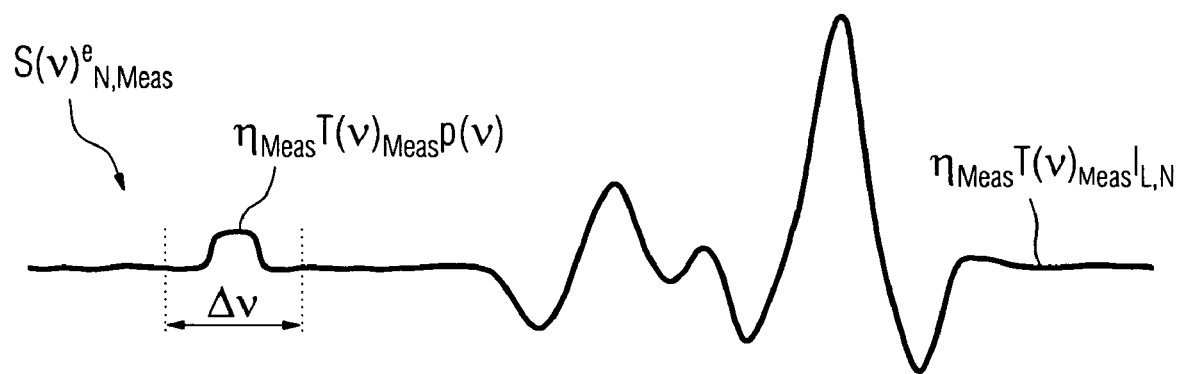
FIG. 2 gives an example for the demodulated measuring detector output containing the measured spectrum and the amplitude envelope of the burst signal.

The measuring detector output containing AC components at the modulation frequency $f_0$ and its higher harmonics $2f_0, 3f_0, 4f_0$, etc. is demodulated at the above mentioned higher harmonic $Nf_0$ in a first demodulation means 20 comprising an analog-to-digital converter 21, a band-pass filter 22, a lock-in amplifier 23 and a phase adjusting means 24 for successively digitizing the measuring detector output, then band-pass filtering the digitized measuring detector output with an $Nf_0$ center frequency in order to eliminate any residual amplitude modulation at $f_0$, converting it to base band and then phase adjusting the lock-in amplifier output. The demodulation at $Nf_0$ shifts the measurement from frequencies near DC, where the light source 2 is noisy, into a higher frequency range, where the noise is lower, thus improving the measurement sensitivity. The in-phase component of the measuring detector output demodulated at $Nf_0$ can be written as:

$$S(v)_{N,Meas}^e = \quad \text{(Equation 8)}$$

$$\eta_{Meas} T(v)_{Meas} \left[ -\alpha_0 L \begin{pmatrix} \chi_N^e I_{L,0}(v_c) + \\ \dfrac{\chi_{N-1}^e + \chi_{N+1}^e}{2} \kappa_1 v_a \cos\phi_1 \\ p(v) + I_{L,N} \end{pmatrix} + \right],$$

where $p(v)$ is the amplitude envelope of the burst signal and $I_{L,N}$ is the laser base line at the $Nf_0$ harmonic. FIG. 2 shows an example for the demodulated measuring detector output $S(v)_{N,Meas}^e$ containing the measured spectrum and the amplitude envelope $p(v)$ of the burst signal.

The light 1 of the diode laser 2 is split by means of a beam splitter 25 in one portion to the measurement path 3 and another portion to a monitor detector 26. The monitor detector output is fed to a second demodulation means 27 comprising an analog-to-digital converter 28, a band-pass filter 29, a lock-in amplifier 30 and a phase adjusting means 31. As the optical path between the diode laser 2 and the monitor detector 26 is free of light-absorbing gas, equation 8 reduces to the following expression for the in-phase component of the monitor detector output demodulated at $Nf_0$:

$$S(v)_{N,Mon} = \eta_{Mon} T(v)_{Mon} [P(v) + I_{L,N}] \quad \text{(Equation 9)}.$$

Figure 3:
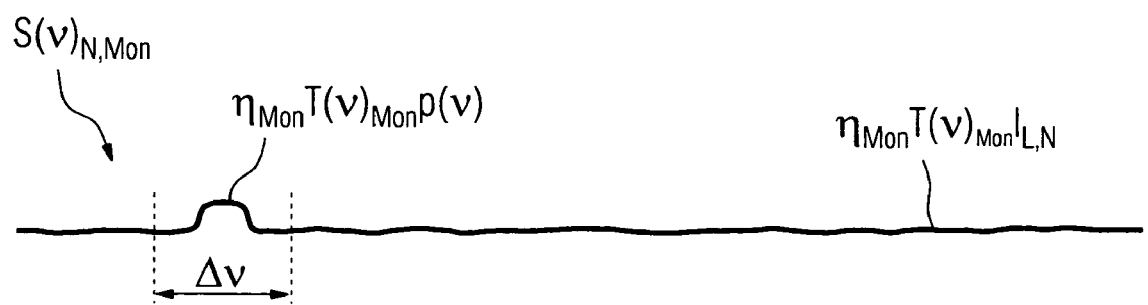
FIG. 3 shows an example for the demodulated monitor detector output.

As shown in FIG. 3 the demodulated monitor detector output $S(v)_{N,Mon}$ will thus contain the amplitude envelope of the burst signal and the down converted transmitted laser base line $I_{L,N}$ revealing any fluctuations caused by non-linearities of the diode laser 2 falling within the detected bandwidth.

The demodulated measuring detector output $S(v)_{N,meas}$ is fed to a multiplication means 32 for multiplying by a variable k, which is continuously calculated in a calculation means 33 as the ratio between the average values of the demodulated monitor detector output $S(v)_{N,Mon}$ and the demodulated measuring detector output $S(v)_{N,meas}$ over a portion $\Delta v$ of the respective demodulated detector outputs where the burst signal appears. The average values can be obtained by integrating the respective demodulated detector outputs over $\Delta v$. As the burst signal is outside the measurement spectrum, one obtains:

$$k = \frac{\int S(V)_{N,Mon} dv}{\int S(v)_{N,Meas} dv} = \frac{\eta_{Mon} T(v)_{Mon}}{\eta_{Meas} T(v)_{Meas}}. \quad \text{(Equation 10)}$$

After multiplication by the variable k the demodulated measuring detector output $k \cdot S(v)_{N,Meas}$ is fed to a subtracting means 34 for subtracting the demodulated monitor detector output $S(v)_{N,Mon}$ and thus obtaining a measurement signal Conc representing the concentration of the gas component associated with the measured molecular absorption line:

$$Conc = \quad \text{(Equation 11)}$$

$$\eta_{Mon} T(v)_{Mon} \alpha_0 L \left[ \chi_N^e I_{L,0}(v) + \frac{(\chi_{N-1}^e + \chi_{N+1}^e)}{2} \kappa_1 v_a \cos\phi_1 \right].$$

As shown by equation 11, the measurement signal Conc is merely dependent on the wavelength independent transmission $T(v)_{Mon}$ between the diode laser 2 and the monitor detector 26, which transmission $T(v)_{Mon}$ is, in contrast to the wavelength independent transmission $T(v)_{Meas}$ of the measurement path 3, not time dependent due to varying dust load, high temperature, gas turbulence etc.

The shown system can be absolutely calibrated in gas concentration by introducing a calibration or reference gas in the measurement path 3. Alternatively, a continuous online calibration can be achieved by splitting another portion of the light 1 emitted by the diode laser 2 through a reference path containing the calibration or reference gas to a reference detector, the output of which is demodulated and further processed as described above for the measuring detector output.

The main advantages realized by this invention are:

The calibration of the light transmission is made at the same frequency as the measurement of the gas concentration avoiding errors due to temporal sample modulation.

The technique utilizes the measurement bandwidth efficiently which reduces the demands on the analog-to-digital converters.

The injected burst signal will be processed in the exactly same manner as the spectra produced by the measured gas why the analog and the digital signal processing components of the system will be included in the calibration.

The invention is easy to implement in existing technology using well-known standard digital signal processing methods. For example, all digital processing can be performed in an ASIC (application specific integrated circuit), DSP (digital signal processor) or FPGA (field programmable gate array).

The invention claimed is:

1. A wavelength modulation spectroscopy method, comprising:
    periodically sweeping the wavelength of a light source over an interaction feature of a sample according to a sweep function;
    modulating the wavelength of the light source with a frequency (f0), while the wavelength is swept over the interaction feature;
    modulating the wavelength of the light source at a wavelength outside the interaction feature with a burst signal with a higher harmonic (Nf0) of said frequency (f0);
    passing the light of the light source to the sample for interacting and thereafter to a measuring detector;
    demodulating the measuring detector output at said higher harmonic (Nf0) of said frequency (f0);
    passing a portion of the light of the light source to a monitor detector;
    demodulating the monitor detector output at said higher harmonic (Nf0) of said frequency (f0); and
    calibrating the demodulated measuring detector output (S(v)N,Meas) against the demodulated monitor detector output (S(v)N,Mon) by the burst signal appearing in both demodulated detector outputs (S(v)N,Meas, S(v)N,Mon), respectively.

2. The method according to claim 1, wherein modulating the wavelength of the light source at a wavelength outside the interaction feature with a burst signal with a higher harmonic (Nf0) of said frequency (f0) is performed periodically.

3. The method according to claim 1, wherein calibrating the demodulated measuring detector output against the demodulated monitor detector output comprises:
    determining the ratio (k) between the average values of the demodulated monitor detector output (S(v)N,Mon) and the demodulated measuring detector output (S(v)N,Meas) over a portion ($\Delta v$) of the respective demodulated detector outputs outputs (S(v)N,Meas, S(v)N,Mon) where the burst signal appears;
    multiplying the demodulated measuring detector output (S(v)N,Meas) by the ratio (k); and
    subtracting therefrom the demodulated monitor detector output (S(v)N,Mon).

4. The method according to claim 3, wherein the respective demodulated detector outputs (S(v)N,Meas, S(v)N,Mon) are integrated over the portion ($\Delta v$) to obtain their average values.

5. A wavelength modulation spectroscopy system, comprising:
    a wavelength tunable light source;
    a first modulation mechanism for periodically sweeping the wavelength of a light source over an interaction feature of a sample according to a sweep function;

a second modulation mechanism for modulating the wavelength of said light source with a frequency (f0), while the wavelength is swept over the interaction feature;

a third modulation mechanism for periodically modulating the wavelength of said light source at a wavelength outside the interaction feature with a burst signal with a higher harmonic (Nf0) of said frequency (f0);

a measuring detector for detecting the light of the light source after interaction with a sample and producing a measuring detector output;

a first demodulation mechanism for demodulating the detector output at a higher harmonic (Nf0) of said frequency (f0);

a monitor detector for detecting the light of the light source and producing a monitor detector output;

a second demodulation mechanism for demodulating the monitor detector output at said higher harmonic (Nf0) of said frequency (f0); and a calibration mechanism for calibrating the demodulated measuring detector output (S(v)N,Meas) against the demodulated monitor detector output (S(v)N,Mon) by the burst signal appearing in both demodulated detector outputs (S(v)N,Meas, S(v)N,Mon), respectively.

6. The system according to claim 5, wherein the calibration mechanism further comprises:

a calculation mechanism for determining the ratio (k) between the average values of the demodulated monitor detector output (S(v)N,Mon) and the demodulated measuring detector output (S(v)N,Meas) over a portion ($\Delta v$) of the respective demodulated detector outputs (S(v)N,Meas, S(v)N,Mon) where the burst signal appears;

a multiplication mechanism for multiplying the demodulated measuring detector output (S(v)N,Meas) by the ratio (k); and a subtracting mechanism for subtracting therefrom the demodulated monitor detector output (S(v)N,Mon).

* * * * *